United States Patent [19]
Neuwirth

[11] Patent Number: 5,891,457
[45] Date of Patent: Apr. 6, 1999

[54] INTRAUTERINE CHEMICAL NECROSING METHOD, COMPOSITION, AND APPARATUS

[76] Inventor: Robert S. Neuwirth, 400 Gloucester St., Englewood, N.J. 07631

[21] Appl. No.: 854,604

[22] Filed: May 12, 1997

[51] Int. Cl.⁶ .............................. A61F 6/06; A61M 31/00
[52] U.S. Cl. ........................ 424/430; 128/831; 128/832; 128/833; 604/55; 604/56
[58] Field of Search ............................ 424/430; 128/831, 128/832, 833; 604/55, 56

[56] References Cited

U.S. PATENT DOCUMENTS

| | | |
|---|---|---|
| 1,652,954 | 12/1927 | Pierce . |
| 2,190,384 | 2/1940 | Newman . |
| 2,355,231 | 8/1944 | Moore . |
| 3,174,481 | 3/1965 | Seaman . |
| 3,394,705 | 7/1968 | Abramson . |
| 3,459,175 | 8/1969 | Miller . |
| 3,540,451 | 11/1970 | Zemma . |
| 3,803,308 | 4/1974 | Zipper et al. . |
| 3,817,248 | 6/1974 | Buckles et al. . |
| 3,822,702 | 7/1974 | Bolduc . |
| 3,848,602 | 11/1974 | Gutnick . |
| 3,875,939 | 4/1975 | Bolduc et al. . |
| 3,887,112 | 6/1975 | Bolduc et al. . |
| 3,924,628 | 12/1975 | Droegemueller et al. . |
| 3,948,259 | 4/1976 | Bolduc et al. . |
| 3,964,477 | 6/1976 | Ellis et al. . |
| 3,972,331 | 8/1976 | Bolduc et al. . |
| 4,012,839 | 3/1977 | Hill . |
| 4,071,027 | 1/1978 | Meador . |
| 4,109,654 | 8/1978 | Bolduc et al. . |

(List continued on next page.)

FOREIGN PATENT DOCUMENTS

92/19145  11/1992  WIPO .

OTHER PUBLICATIONS

Nechay et al., "Inhibition of Adenosine Triphosphates In Vitro By Silver Nitrate Silver Sulfadiazine", Journal of Environmental Pathology, Toxicology, and Oncology, vol. 5, No. 4–5, pp. 119–126 (1984).

Nechay et al., "Inhibition of Adenosine Triphosphatases In Vitro By Silver Nitrate And Silver Sulfadiazine", Journal of the American College of Toxicology, vol. 3, No. 1, pp. 37–42 (1984).

Williams et al., "Chemical Injury of Arteries", Journal of Pathology and Bacteriology, vol. 77, pp. 63–69 (1959).

No author, Silver nitrate wart treatment available OTC; Launches Avoca, a silver nitrate pencil for wart removal, Chemist & Druggist, 1994 Jul. 16, p. 38 (1994).

No author, "Novel Biocide Design Using an Inorganic Composite", Speciality Chemicals, 1994 Jun., p. 223 (1994).

No author, "Spectrum Chemical and Safety Products", pp. S–xii, C–392–C–393 (1993–1994).

Richart et al., "Single–application fertility–regulating device: Description of a new instrument", Obstet. Gynecol. 127:86, 1977.

(List continued on next page.)

Primary Examiner—Carlos A. Azpuru
Attorney, Agent, or Firm—Kenyon & Kenyon

[57] ABSTRACT

A method and composition for effecting chemical necrosis of a tissue lining of a mammalian body cavity, particularly a uterine endometrium, by delivering a caustic tissue necrosing composition, e.g., a silver nitrate and dextran paste, to the tissue to be necrosed and allowing the paste to remain in contact with the target tissue for a period of time sufficient to chemically necrose substantially the entirety of the tissue lining, and then contacting the caustic composition with a deactivating agent, e.g., an aqueous sodium chloride solution, thereby rendering the caustic composition non-caustic, and then rinsing the cavity. Compositions and methods for delivering medicaments are also disclosed.

30 Claims, 4 Drawing Sheets

U.S. PATENT DOCUMENTS

| | | |
|---|---|---|
| 4,119,098 | 10/1978 | Bolduc et al. |
| 4,126,134 | 11/1978 | Bolduc et al. |
| 4,137,922 | 2/1979 | Leininger et al. |
| 4,160,446 | 7/1979 | Barrington |
| 4,293,536 | 10/1981 | Jensen et al. |
| 4,430,076 | 2/1984 | Harris |
| 4,585,438 | 4/1986 | Makler |
| 4,601,698 | 7/1986 | Moulding, Jr. |
| 4,637,818 | 1/1987 | Johnson et al. |
| 4,773,899 | 9/1988 | Spears |
| 4,857,555 | 8/1989 | Smith et al. |
| 4,863,932 | 9/1989 | Sinensky et al. |
| 4,891,043 | 1/1990 | Zeimer et al. |
| 5,030,202 | 7/1991 | Harris |
| 5,039,704 | 8/1991 | Smith et al. |
| 5,063,065 | 11/1991 | Bazterrica et al. |
| 5,100,388 | 3/1992 | Behl et al. |
| 5,104,377 | 4/1992 | Levine |
| 5,105,808 | 4/1992 | Neuwirth et al. |
| 5,163,905 | 11/1992 | Michael |
| 5,170,774 | 12/1992 | Heckele |
| 5,174,304 | 12/1992 | Latina et al. |
| 5,188,602 | 2/1993 | Nichols |
| 5,192,688 | 3/1993 | Switzer, III et al. |
| 5,195,965 | 3/1993 | Shantha |
| 5,242,390 | 9/1993 | Goldrath |
| 5,242,437 | 9/1993 | Everett et al. |
| 5,256,139 | 10/1993 | Ghodsian |
| 5,257,977 | 11/1993 | Eshel |
| 5,279,542 | 1/1994 | Wilk |
| 5,282,785 | 2/1994 | Shapland et al. |
| 5,286,254 | 2/1994 | Shapland et al. |
| 5,290,763 | 3/1994 | Poser et al. |
| 5,298,018 | 3/1994 | Narcisco, Jr. |
| 5,300,023 | 4/1994 | Lowery et al. |
| 5,304,214 | 4/1994 | DeFord et al. |
| 5,306,249 | 4/1994 | Michel |
| 5,364,375 | 11/1994 | Swor |
| 5,371,191 | 12/1994 | Poser et al. |
| 5,372,584 | 12/1994 | Zink et al. |
| 5,380,317 | 1/1995 | Everett et al. |
| 5,397,803 | 3/1995 | Smith et al. |
| 5,403,309 | 4/1995 | Coleman et al. |
| 5,403,311 | 4/1995 | Abele et al. |
| 5,423,807 | 6/1995 | Milder |
| 5,431,662 | 7/1995 | Nicholas |
| 5,433,708 | 7/1995 | Nichols et al. |
| 5,434,247 | 7/1995 | Jones |
| 5,435,805 | 7/1995 | Edwards et al. |
| 5,437,660 | 8/1995 | Johnson et al. |
| 5,445,961 | 8/1995 | Genovesi et al. |
| 5,451,208 | 9/1995 | Goldrath |
| 5,453,086 | 9/1995 | Weber |

OTHER PUBLICATIONS

Paul et al., "Transvaginal Human Sterilization: A Preliminary Report", ASC Symposium Series 33, American Chemical Society, Washington, D.C., 1976.

Gregor et al., "Fallopian Tube Cauterization by Silver Ion–Polymer Gels", Controlled Release Polymeric Formulations, pp. 147–156.

Thompson et al., "Evaluation of Experimental Methods of Occluding the Uterotubal Junction", Female Sterilization (Prognosis for Simplified Outpatient Procedures), Academic Press, 1972, pp. 107–123.

Martens, F., "Attempted Cyrosurgical Closure of the Fallopian Tubes", Human Sterilization (A Conference), Charter 26, pp. 305–312, Charles C. Thomas, Springfield, Ill.

Stevenson et al., "The Effect of Methyl Cyanoacrylate Tissue Adhesive on the Human Fallopian Tube and Endometrium," The Journal of Obstetrics and Gynaecology of the British Commonwealth, Nov. 1972, vol. 79, pp. 1028–1039.

Mullick et al., "Studies of Quinacrine and of Tetracycline for Non–surgical Female Sterilization", Indian Rural Medical Association, Adv Contracept (England), Sep. 1987, pp. 245–254.

Benoit et al., "Chemically Induced Tubal Occlusion in the Human Female Using Intrauterine Instillation of Quinacrine", Contraception (United States), Jul. 1975, pp. 95–101.

Bhatt et al., "Four Year Follow Up of Insertion of Quinacrine Hydrochloride Pellets as a Means of Nonsurgical Female Sterilization", Fertil Steril (United States), Sep. 1985, pp. 303–306.

Chandra, "Toxic Effects of Quinacrine Hydrochloride in Rhesus Monkeys", Contraception (United States), Sep. 1981. pp. 269–274.

Ciaccio et al., "Observation on Toxic Effects of Quinacrine Hydrochloride (in rodents)", Contraception (United States), Mar. 1978, pp. 231–236.

Dubin et al., "Effect of Intrauterine Administration of Tetracyclines on Cynomolgus Monkeys", Contraception (United States), Jun. 1984, pp. 561–571.

Dubin et al., "Comparative Effects of Intrauterine Instillation of Analogues of Quinacrine and Tetracycline on Uterine Morphology in the Rat", Contraception (United States), Jun. 1984, pp. 553–559.

Dubin et al., "Effect of Intrauterine and Intravascular Quinacrine Administration of Histopathology, Blood Chemistry, and Hematology in Cynomolgus Monkeys", Fertil Steril (United States), Dec. 1982, pp. 741–747.

Dubin et al., "Pharmacokinetic Studies on Quinacrine Following Intrauterine Administration to Cynomolgus Monkeys", Fertil Steril (United States), Dec. 1982, pp. 735–740.

el–Kady, et al., "Histopathologic Changes in the Cornual Portion of the Fallopian Tube Following a Single Transcervical Insertion of Quinacrine Hydrochloride Pellets", Department of Obstetrics and Gynecology, Boulak El–Dakrour Hospital, Giza, Egypt.

Laufe et al., "Nonsurgical Female Sterilization", Int J Gynaecol Obstet (United States), 1980, pp. 334–339.

Merchant et al., "Clinicopathologic Study of Fallopian Tube Closure After Single Transcervial Insertion of Quinacrine Pellets", Obstetrics and Gynecology, B.Y.L. Nair Hospital, Bombay, India, Int J Fertil Menopausal Stud (United States), Jan.–Feb. 1995, pp. 47–54.

Mukherjee et al., "Fluorescence of X and Y Chromatin in Human Interphase Cells", Cytogenetics (Switzerland), 1972, pp. 216–227.

Patek, "Quinacrine Hydrochloride. Review and Mode of Action of an Antimalarial, Used as an Occlusive Agent for Transvaginal Human Sterilzation", Acta Obstet Gynecol Scand (Sweden), 1979, pp. 561–564.

Pollack et al., "Association for Voluntary Surgical Contraception: A Technical Statement on Quinacrine Pellets for Nonsurgical Female Sterilization", Association for Voluntary Surgical Contraception, New York, NY 10016, Adv Contracept (Netherlands), Mar. 1994, pp. 43–50.

Raman et al., "Endometrial Enzyme Activity in Rats Instilled with Quinacrine Hydrochloride", Indian J Exp Biol (India), Oct. 1978, pp. 1074–1075.

Schenker et al., "Regeneration of Rabbit Endometrium Following Intrauterine Instillation of Chemical Agents", Gynecol Invest (Switzerland), 1973, pp. 1–13.

Zaneveld et al., "Lack of Tubal Occlusion by Intrauterine Quinacrine and Tetracycline in the Primate", Contraception (United States), Aug. 1984, pp. 161–167.

Zimmerman et al., "Antifertility Effects of Tetradecyl Sodium Sulphate in Rabbits", J Reprod Fertil (England), Jul. 1983, pp. 257–263.

Zook et al., "Malignant Neoplasms of Decidual Origin (Deciduosarcomas) Induced by Estrogen–Progestin–Releasing Intravaginal Device in Rabbits", Am J Pathol (United States), Aug. 1987, pp. 315–327.

Dubin et al., "Intrauterine Ethanol–Induced Termination of Pregnancy in Cynomolgus Monkeys (*Macaca fascicularis*)", Am J Obstet Gynecol (United States), Dec. 1, 1978, pp. 783–790.

Franke et al., "Electron Microscopic Studies in the Fine Structure of the Visceral Yolk Sac Epithelium of the Rat Following an Intrauterine Injection of Rabbit Antirat Placental Serum or Normal Rabbit Serum", Beitr Pathol (Germany, West), 1973, pp. 1–14.

Frazer et al., "Histopathologic Effects of Dimethyl Sulfoxide on Equine Endometrium", Department of Veterinary Clinical Sciences, College of Veterinary Medicine, Ohio State University, Columbus 43210, Am J Vet Res (United States), Oct. 1988, pp. 1774–1781.

Boto et al., "Surgical Alternatives to Hysterectomy for Intractable Menorrhagia", British Journal of Hospital Medicine, vol. 44, Aug. 1990, pp. 94–99.

Corfman, "Transcervical Oviduct Occlusion", Acting Director, Reproduction Program, National Institute of Child Health and Human Development, United States Public Health Service, Washington, D.C., pp. 183–187.

Corfman et al., "Response of the Rabbit Oviduct to a Tissue Adhesive", Science, vol. 14, Jun. 1965, pp. 1348–1350.

Corfman et al., "An Instrument for Transcervical Treatment of the Oviducts and Uterine Cornua", Obstetrics & Gynecology, vol. 27, No. 6, Jun. 1996.

DeCherney et al., "Endometrial Ablation for Intractable Uterine Bleeding: Hysteroscopic Resection", Obstetrics & Gynecology, vol. 70, No. 4, Oct. 1987, pp. 668–670.

Davis et al., "Fallopian Tube Occlusion in Rabbits with Silicone Rubber", The Journal of Reproductive Medicine, vol. 14, No. 2, Feb. 1975, pp. 56–61.

Droegemueller et al., "Cryocoagulation of the Endometrium at the Uterine Cornua", American Journal of Obstetrics and Gynecology, vol. 131, No. 1, May 1, 1978, pp. 1–9.

Dubin et al., "Effect of Intrauterine and Intravascular Quinacrine Administration on Histopathology, Blood Chemistry, and Hematology in Cynomolgus Monkeys", Fertility and Sterility, vol. 38, No. 6, Dec. 1982, pp. 741–747.

Goldrath et al., "Intrauterine Laser Surgery", Chapter 8, pp. 93–110.

Hill et al., "Intrauterine Surgery Using Eletrocautery", Aust NZ J Obstet Gynaecol, 1990, pp. 145–146.

Imlach, "Edmonton Gynecologist at Legal Odds with Provinicial College", CMA Journal, Jun. 7, 1975, vol. 112, pp. 1348 and 1355.

Laufe et al., "Nonsurgical Female Sterilization", Int J Gynaecol Obstet, vol. 18, 1980, pp. 333–339.

Magos, "Management of Menorrhagia", BMJ, vol. 300, Jun. 16, 1990, pp. 1537–1538.

Martin et al., "An Alternative to Hysterectomy Endometrial Laser Ablation", The British Journal of Theatre Nursing, May 1990, pp. 10–11.

Neuwirth et al., "Chemical Induction of Tubal Blockade in the Monkey", Obstetrics & Gynecology, vol. 238, No. 1, Jul. 1971, pp. 51–54.

Omran et al., "Tubal Occlusion: A Comparative Study", International Journal of Fertility, Oct.–Dec. 1970, vol. 15, No. 4, pp. 226–244.

Phipps et al., "Treatment of Functional Menorrhagia by Radiofrequency–Induced Thermal Endometrial Ablation", The Lancet, Feb. 17, 1990, 374–376.

Pitkin, "Sodium Morrhuate for Tubal Sterilization", Obstetrics & Gynecology, vol. 28, No. 5, Nov. 1966, pp. 680–683.

Richart, "Female Sterilization Using Chemical Agents", Research Frontiers in Fertility Regulation, Dec. 1981, vol. 1, No. 5, pp. 1–12.

Richart et al., "Female Sterilization by Electrocoagulation of Tubal Ostia Using Hysteroscopy", Am. J. Obstet. Gynecol., Nov. 15, 1973, pp. 801–804.

Ringrose, "Office Tubal Sterilization", Obstetrics & Gynecology, vol. 42, No. 1, Jul. 1973, pp. 151–155.

Richart, "The Use of Chemical Agents in Female Sterilization", Female Transcervical Sterilization, pp. 24–34.

Zipper et al., "Alterations in Fertility Induced by Unilateral Intrauterine Instillation of Cytotoxic Compounds in Rats", Am. J. Obst. & Gynce., Aug. 1, 1968, pp. 971–978.

Zipper et al., "Intrauterine Instillation of Chemical Cytotoxic Agents for Tubal Sterilization and Treatment of Functional Metrorrhagias", International Journal of Fertility, Oct.–Dec. 1969, vol. 14, No. 4, pp. 280–288.

Zipper et al., "Human Fertility Control by Transvaginal Application of Quinacrine on the Fallopian Tube", Fertility and Sterility, vol. 21, No. 8, Aug. 1970, pp. 581–589.

Laufe et al., "Nonsurgical Female Sterilization", Int J Gynaecol Obstet (United States), 1980, pp. 334–339.

Richart et al., "Intrauterine Administration of Methyl Cyanoacrylate as an Outpatient Method of Permanent Female Sterlization", Am J Obstet Gynecol (United States), Apr. 1987, pp. 981–987.

Steveson et al., "The Effect of Methyl Cyanoacrylate Tissue Adhesive on the Human Fallopian Tube and Endometrium", J Obstet Gynaecol Br Commonw (England), Nov. 1972, pp. 1028–1039.

No author, The Use of Methyl Cyanoacrylate (MCA) for Female Sterilization, Program for Applied Research on Fertility Regulation Northwestern University Medical School, Chicago, Illinois, Contraception (United States), Mar. 1985, pp. 243–252.

Scroggs et al., "Acid Hematin Pigemtation of the Cornea in Stillborn Fetuses", Department of Pathology, Duke University Medical Center, Durham, North Carolina 27710.

Saraga et al., "The Prune Belly Syndrome", Acta Med Iugosl (Yugoslavia), 1989, pp. 223–233.

Dubin et al., "Effects of Silver Nitrate on Pregnancy Termination in Cynomolgus Monkeys", Fertil. Steril., Jul. 1981, pp. 106–109.

Guenther et al., "The Apparent Molar Dilution of Precipitation Reactions Exemplified by the Reaction of Sodium Chloride and Silver Nitrate in Aqueous Solution", Zeitshcriff fuer Physikalische Chemie Neue Folge, pp. 24–37 (1973).

INTRAUTERINE CHEMICAL NECROSING METHOD, COMPOSITION, AND APPARATUS

BACKGROUND OF THE INVENTION

1. Field of the Invention

This invention relates to methods, compositions, and apparatus for chemically necrosing the tissue lining of a human body cavity, particularly the endometrium of the uterus. More specifically, the methods, compositions, and apparatus of the present invention provide effective chemical necrosis of the endometrium of a mammalian uterus so as to treat menorrhagia and encourage amenorrhea without many of the disadvantages and dangerous features of known intrauterine necrosing techniques.

2. The Prior Art

The following terms as used herein have the meaning given below:

"Necrosis" means the death of cells in a tissue.

"Endometrium" is that portion of the inner lining of the uterus to which an embryo normally attaches and excludes the portions of the uterine inner lining forming the cervix, to which the embryo usually does not attach.

"Cryogenic" is used to refer to temperatures sufficiently low to cause necrosis.

"Caustic Agent" or "caustic paste" is an agent capable of effecting necrosis of the cells in a tissue, e.g., the tissue lining a body cavity such as the uterus.

"Chemical Necrosis" is necrosis resulting from contact with a caustic agent.

"Deactivating Agent," "washout solution," and "washout lotion" means any agent capable of rendering a caustic agent or caustic paste non-caustic.

"Menorrhagia" means heavy menstrual bleeding, i.e., in excess of about 80 ml of blood loss per month.

Apparatus and methods for necrosing of the endometrium of a mammalian uterus, useful in sterilization procedures and cancer treatments, are well known. Thermal and cryogenic treatments have been utilized in such necrosing techniques and typically involve either the direct or indirect application of heat or cold to the tissue to be treated.

For example, a laser hysteroscope has been used to necrose the endometrial layer of the uterus. This laser treatment suffers from several disadvantages. It requires the application of an intense amount of thermal energy to a relatively small area of tissue even though such a large amount of heat may not be necessary to effectively necrose the tissue. Further, this laser treatment requires the physician to continually re-position the laser under hysteroscopic control used in the treatment within the uterus in order to treat the entire endometrium. Such internal manipulation of a laser hysteroscope within the uterus of a patient is both difficult, requiring a significant level of skill to perform, and potentially dangerous. Accidental puncture of the uterine or tissue wall may result from manipulation of the laser scope within the uterus or body cavity, and tissue layers beneath the endometrium may be burned through the entire thickness if a laser's beam is left focused on one area of tissue for too long a period of time. Electrosurgical endometrial necrosis functions on a similar principle and suffers similar risks as laser endometrial necrosis.

A variety of alternatives to laser treatment in necrosing the uterine endometrium are known. In U.S. Pat. Nos. 4,949,718 and 5,105,808 to Neuwirth et al. a method and device for effecting the necrosis of the tissue lining of a mammalian body cavity, particularly the uterine endometrium by heating the liquid contents of an inflated distendable bladder inside the uterine cavity is disclosed. Inflating the distendable bladder inside the uterus allows for contact between the distendable bladder wall and the endometrial lining.

U.S. Pat. No. 3,924,628, to Droegemueller et al. discloses a method and apparatus for necrosing tissue cells that utilizes an extendable bladder which is inserted in the uterus and filled with a circulating fluid or gas at cryogenic temperatures (referring to temperatures sufficiently low to cause cell necrosis). The bladder disclosed by Droegemueller et al. is maintained in substantially continuous contact with the inner surface of the uterine lining and achieves necrosis of substantially all of the uterine endometrium in a single treatment. Droegemueller et al. disclose the use of liquid nitrogen that vaporizes prior to introduction into the bladder, thereby pressurizing the bladder to a level which ensures adequate contact with the uterus. Other fluids disclosed by Droegemueller et al. as useful in their method include refrigerants such as freon. Droegemueller et al.'s method and apparatus suffers from the disadvantage of employing cryogenic fluids which are toxic and could prove fatal to a patient in the event of bladder rupture. Moreover, Droegemueller et al.'s apparatus does not allow regulating the pressure used to inflate the bladder. In the event of a bladder rupture, the cryogenic fluid would rapidly change state from a liquid to a gas with possible grave consequences for the patient. Another disadvantage of Droegemueller et al.'s technique is that it does not limit the amount of cryogenic fluid that would be introduced into the uterus in the event of a bladder rupture.

In U.S. Pat. No. 2,734,508, Kozinski discloses a therapeutic apparatus for applying dry heat to body cavities comprising an applicator that is introduced in the body cavity while deflated and which is subsequently inflated and heated by means of circulating hot air. Kozinski does not disclose an applicator which conforms to the shape of a body cavity. Further, given the lower heat transfer coefficients of gases as compared with liquid, treatment with Kozinski's apparatus should involve a long period of time in order to achieve necrosis, thereby exposing the patient to additional discomfort and risk. Moreover, Kozinski's apparatus does not provide for measurement and regulation of internal pressures and temperatures of the applicator introduced.

U.S. Pat. No. 2,077,453, issued to Albright, discloses a therapeutic appliance comprising a relatively long tubular applicator which is shaped and formed generally to the passage into which it is to be inserted and which has relatively thin elastic rubber walls that transfer heat and which distend to fit irregularities of the treated areas upon application of internal pressure. Albright also discloses that fluids such as heated water could be utilized as a heating means in his applicator. The applicator of Albright, like that of Kozinski, however, suffers from the disadvantage that the distension of its walls to conform to the irregularities of the endometrium is limited as Albright provides an integral rubber web which serves to prevent undue distension of the applicator. Moreover, Albright requires that the fluid be circulated throughout the apparatus. Albright also does not provide an apparatus that allows regulation of temperature and pressure of the fluid or other bladder inflation means.

U.S. Pat. No. 3,369,549, issued to Armao, discloses a therapeutic device for applying heat or cold to body cavities comprising a capsule probe containing a heat exchanger and a flexible bladder that can be inflated to conform to a body cavity. Armao does not, however, disclose a control means for regulating the temperature and pressure of the flexible applicator, nor does he disclose necrosing tissue in the cavity being treated.

Other patents that disclose the use of thermal treatment of the interior lining of a body cavity include U.S. Pat. Nos. 2,192,768; 2,466,042; 2,777,445; and 3,369,549.

In addition to these thermal and cryogenic treatments, application of caustic chemicals within the human body to achieve sterilization and treat cancers is also known. The use of caustic chemicals as locally destructive agents has been attempted but has been limited by concerns about safety and control of the delivery of various agents as well as other shortcomings due to the methods of application, e.g., blind placement of a particular solid chemical. For example, as described by Babcock, W., *Chemical Hysterectomy*, Jnl. Obstet. & Gyn., Vol. 7, p. 693 (1924), application of gauze strips soaked in a saturated solution of zinc chloride to the uterine walls has reportedly been used to produce amenorrhea, to produce sterility, and to treat tumors. However this procedure has several disadvantages. Initially, it is noted that the application of the gauze strips is a blind procedure. The zinc chloride soaked gauze is packed in the uterus until the practitioner feels the cavity is full. The strips are left in place for a predetermined length of time and then removed. Delivery to and removal from the uterine cavity of the caustic gauze strips necessarily entails substantial risk of contacting the vaginal walls wherein the caustic could damage the vaginal and other tissue which is not the target of the treatment. Accordingly, successful use of this methodology requires substantial skill and experience, limiting the availability of the procedure to women with access to highly trained medical personnel.

Use of caustic agents such as silver nitrate, zinc chloride and copper sulfate has been studied for use in chemical sterilization by chemically cauterizing the fallopian tubes. However, as discussed by Richart, R., *Female Transcervical Sterilization*, Chapter 3, Harper & Row (1983), even when massive tubal necrosis was achieved with the application of silver nitrate ($AgNO_3$), a significant proportion of fallopian tubes remained open. When compositions for the sustained release of the caustic agents were employed it was found that control over the release of the caustic agents was insufficient to avoid unacceptable side effects. Additionally, use of strong caustic agents such as acids and alkalies would require the concomitant use of equally strong neutralizing agents whose use is also laden with risk. Use of such agents also puts the practitioner in the difficult position of titrating the neutralization of the caustic agent in the patient's uterus.

SUMMARY AND OBJECTS OF THE INVENTION

It is an object of the present invention to provide a safe and efficacious method for chemically necrosing the tissue lining of a body cavity, particularly the endometrium of a human uterus, utilizing a caustic agent capable of chemically necrosing target tissue to a desired depth in a reasonable amount of time and wherein the caustic agent can be selectively and rapidly rendered non-caustic by contact with a deactivating agent. In an especially preferred embodiment the deactivating agent is innocuous, i.e., not harmful to human tissue.

It is another object of the present invention to provide a relatively inexpensive and easy to use paste composition of a caustic agent and a non-toxic carrier, which is easily and safely deactivated by a deactivating agent, that can be used to effect chemical necrosis of lining of a mammalian body cavity.

It is still another object of the present invention to provide a method for introducing a controlled amount of caustic agent under predetermined pressure into a uterine cavity so as to increase the likelihood of the silver nitrate making substantially uniform and intimate contact of the paste with the endometrium for a predetermined time without passage into the peritoneal cavity.

It is another object of the present invention to provide a method for effecting chemical necrosis of the tissue lining of a mammalian body cavity comprising the steps of inserting a hysteroscope into the body cavity; passing a fluid medium through the hysteroscope to expand the body cavity, wherein the fluid medium is not a deactivating agent, e.g., an inert gas or non-electrolyte liquid; applying to the tissue to be treated a caustic composition, spreading the caustic paste substantially uniformly over the tissue surface while under observation through the hysteroscope so that the paste is in contact with substantially all of the tissue lining for which necrosis is desired; allowing the caustic paste to remain in the body cavity for a period of time sufficient to effect chemical necrosis of substantially all of the tissue lining of the body cavity for which necrosis is desired; introducing a deactivating agent to the tissue lining for deactivating the caustic agent and removing the deactivated caustic agent and the deactivating agent from the body cavity; and removing the hysteroscope.

It is yet another object of the present invention to provide a method for effecting chemical necrosis of the tissue lining of a mammalian uterus comprising the steps of inserting a hysteroscope into the uterus; passing $CO_2$ gas through the hysteroscope to expand the uterus; passing through the hysteroscope a first catheter for delivery of a predetermined volume of silver nitrate paste and a second catheter for delivery of an aqueous sodium chloride solution for deactivating the silver nitrate paste; spreading the silver nitrate paste substantially uniformly over the endometrium while under observation through the hysteroscope so that the paste is in contact with substantially all of the lining of the endometrium; allowing the $CO_2$ gas used to expand the uterus to exit the uterus returning the uterus to its relaxed state thereby further aiding in the distribution of the silver nitrate paste over the endometrial surface as the uterus contracts; allowing the silver nitrate paste to remain in the uterus for a period of time sufficient to effect chemical necrosis of substantially all of the endometrial lining of the uterus; delivering to the uterus through the second catheter an aqueous sodium chloride solution for deactivating the silver nitrate paste to substantially inert silver chloride; and rinsing the silver chloride from the uterus by tidal flow or continuous sodium chloride rinsing or irrigation washing.

It is still another object of the present invention to provide a method for effecting chemical necrosis of the tissue lining of a mammalian body cavity comprising the steps of inserting a catheter into the body cavity; delivering a caustic paste through the catheter into the body cavity to the natural fill volume of the body cavity, not to exceed a predetermined volume and/or pressure; regulating the pressure of the caustic paste by control means connected to the catheter; and maintaining the paste so inserted for a period of time sufficient to effect chemical necrosis of substantially all of the tissue lining of the body cavity for which necrosis is desired; introducing a deactivating solution for deactivating the caustic to substantially inert non-caustic components and removing the deactivated caustic from the body cavity via tidal flow or continuous sodium chloride rinsing or irrigation washing.

The present invention also provides a method for effecting chemical necrosis of the endometrium of a mammalian uterus comprising the steps of inserting first and second catheters, or a multlumen catheter into the uterus; delivering between approximately 5 ml and 15 ml of a silver nitrate paste into the uterus not to exceed the natural fill volume of the uterus through the first catheter, not to exceed a predetermined pressure which should be below fallopian tubal opening pressure; controlling the pressure of the silver nitrate paste; and maintaining the silver nitrate paste so inserted for a period of time sufficient to effect chemical necrosis of substantially all of the uterine endometrium; delivering to the uterus through the second catheter, or lumen, an aqueous sodium chloride solution for deactivating the silver nitrate to substantially inert silver chloride, and rinsing the silver chloride from the uterus.

The present invention also provides a method for treating menorrhagia, comprising the steps of applying a caustic composition to the endometrium of a uterus; allowing the caustic composition to remain in contact with the endometrium for a period of time sufficient to effect chemical necrosis of the endometrium; contacting the caustic composition with a deactivating agent to deactivate the caustic composition; and withdrawing the deactivated caustic composition and the deactivating agent from the uterus.

The present invention also provides a method for treating the endometrium of a uterus, comprising the steps of applying a silver nitrate composition to the endometrium of a uterus; allowing the silver nitrate composition to remain in contact with the endometrium for a period of time sufficient to effect cauterization necrosis of the endometrium; contacting the silver nitrate with a solution of sodium chloride to deactivate the silver nitrate; and withdrawing the deactivated silver nitrate and the sodium chloride from the uterus.

The present invention also provides a composition for treating the endometium of a uterus, comprising about 10% to about 50% by weight silver nitrate; about 35% to about 80% by weight dextran; and about 0% to about 55% weight $H_2O$.

The present invention also provides a composition for treating the endometrium of a uterus, comprising about 43% by weight silver nitrate; about 29% by weight dextran and about 34% by weight $H_2O$.

It is yet another object of this invention to provide a composition for treating the endometrium of a uterus, comprising about 34% by weight silver nitrate; about 31% weight dextran and about 34% by weight $H_2O$.

The present also provides a washout solution or washout lotion for deactivating the caustic paste, comprising about 32% to about 40% by weight dextran and about 60% to about 68% by weight normal saline and having a viscosity of between about 220 to about 660 centipoise.

DETAILED DESCRIPTION OF THE INVENTION

Figure 1:
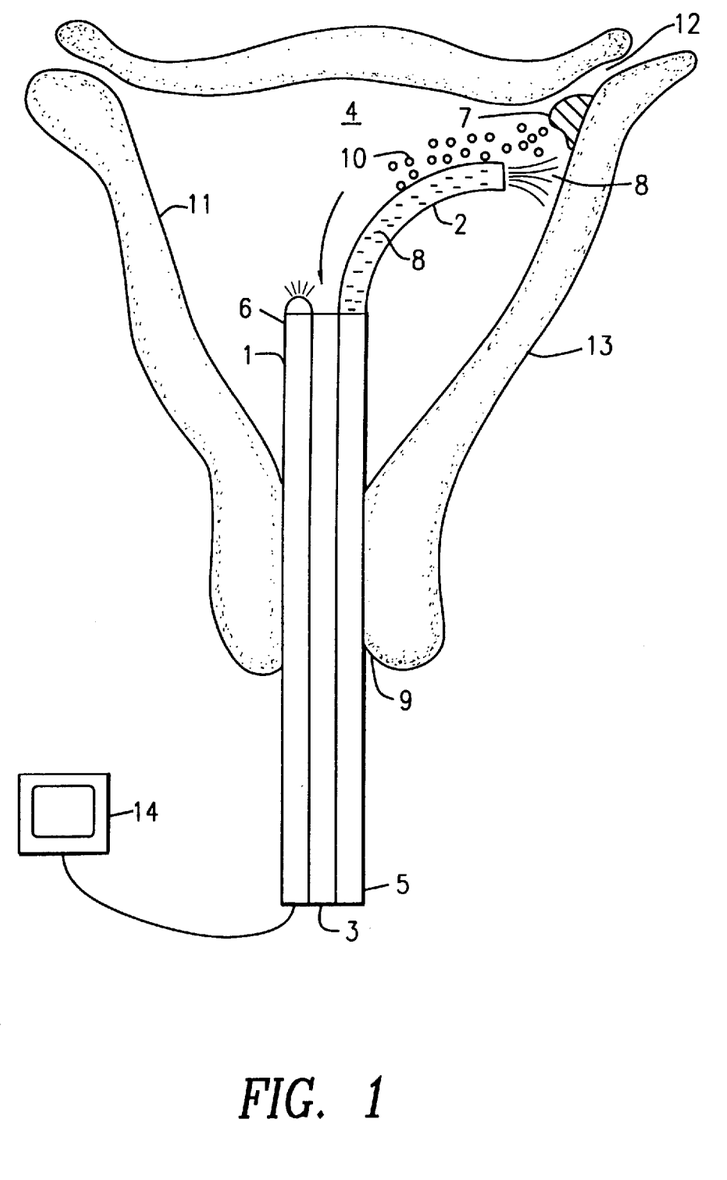
FIG. 1 shows one embodiment of the invention in which a hysteroscope has been inserted into a mammalian uterus.

FIG. 1 shows a hysteroscope 1 provided with passages for first catheter 2 and second catheter 3 passing therethrough. The hysteroscope 1 has a proximal end 5 and a distal end 6 with the distal end 6 being located within the uterine cavity 4 of a mammalian uterus 13. While the external diameter of the hysteroscope 1 must be sufficiently small so that it can be safely and conveniently inserted into the uterine cavity 4 through a partially dilated cervix 9, it must have an internal diameter sufficiently large to accommodate the first and second catheters 2 and 3. The external diameter of the hysteroscope 1 must be sufficiently wide, or expandable, so as to make a substantially air and liquid tight seal with the cervix 9. In order to allow for easy insertion, this seal may be created by employing any one of several devices well known to those skilled in the art such as a contracervical cap, an intracervical balloon, or an intracervical plug. The proximal end 5 of the hysteroscope 1 may be adapted in any one of several ways well-known to those skilled in the art to allow for the free manipulation of the first catheter 2 to provide more accurate delivery of the caustic paste 7 and also allow for the selective delivery of gas or liquid through the second catheter 3 to both expand the uterine cavity 4 before treatment and to flush the uterine cavity 4 with a deactivating agent 8 after treatment.

As shown in FIG. 1, the hysteroscope 1 housing the first catheter 2 and the second catheter 3 is aligned with the cervical canal after the cervix 9 is exposed with a speculum and grasped with a tenaculum. After the hysteroscope 1 has been inserted into the uterine cavity 4, a fluid medium is pumped into the uterine cavity 4 via second catheter 3 to a pressure sufficient to ensure expansion of the uterine cavity 4. The uterus 13 can be thought of as a collapsed body cavity, i.e., a potential body cavity or an undistended uterine cavity. The fluid medium may be, e.g., an inert gas, preferably $CO_2$, or a non electrolyte liquid, or any other biologically acceptable fluid medium that will not deactivate or otherwise react with the caustic agent. This allows the physician to visualize on monitor 14 the application of the caustic agent, e.g., silver nitrate paste 7 to the endometrial tissue layer on the interior endometrial surface of the uterine cavity 4. The pressure of the $CO_2$ should preferably be maintained at a pressure of about 30 to about 50 mmHg, and preferably about 40 mmHg, to maintain the uterus in the expanded state while minimizing the risk of damage to the uterine wall and minimizing the risk of overcoming fallopian tubal opening pressure. The pressure of the $CO_2$ is regulated by an expansion medium pressure control means (not shown). A block could be placed in the openings of the fallopian tubes to reduce the risk of caustic agent 7 entering the tubes 12. The hysteroscope may be removed after the toxic paste has been applied. Alternatively, it may be left in place until after the uterine cavity 4 has been rinsed clear. This allows the physician to hysteroscopically observe the action of the caustic agent 7 and the deactivating agent 8.

After the uterine cavity 4 has been expanded, the caustic paste 7, e.g., silver nitrate, may be applied to the tissue to be treated. The first catheter 2 disposed within the hysteroscope 1 may be extended through an opening located at the distal end 6 of the hysteroscope 1. The delivery of the silver nitrate paste 7 may be accomplished through the first catheter 2, preferably a 2 mm catheter, under hysteroscopic control and preferably in a carbon dioxide gas environment. The paste is a mixture of caustic agent in an amount sufficient to effect chemical necrosis of the target tissue, an inert carrier, and the balance a non-reactive fluid. In a preferred embodiment, the composition comprises about 10 to 50% by weight caustic agent and about 35 to 80% by weight inert carrier to form a fluid paste. In an especially preferred embodiment the paste is about 10 to 50% by weight caustic agent and about 35 to 80% by weight Dextran 70™ or Dextran 40™ and water. Dextran 40™ and Dextran 70™ are manufactured by Pharmacia, Inc. of Piscataway, N.J. Most preferably, the paste is 10 to 50% by weight silver nitrate and 30 to 80% by weight Dextran 70™ or Dextran 40™ and water. Preferably, the paste composition is adjusted to a viscosity suitable for the specific application and the introduction and withdrawal devices used in the process. By increasing the Dextran 70™ or Dextran 40™ to water ratio the paste will become more viscous and may be made more difficult to pass through syringes or catheters with narrow bores. The consistency or viscosity of the paste is adjusted to a thickness that allows control of the flow of the paste within the uterus during the procedure.

The hysteroscope 1 is connected to a monitor 14 which allows the practitioner to observe the procedure and assure that the silver nitrate paste 7 is applied to the target tissue to be treated. The effect of the silver nitrate paste 7 can be observed as is currently done using laser or electrosurgical coagulation of the endometrium using a hysteroscope. After application of the paste 7 is completed, the $CO_2$ distending the uterine cavity 4 is evacuated through second catheter 3 which returns the uterine cavity 4 to its relaxed state. This allows the opposing internal walls 11 of the uterus 13 to contact each other thereby further distributing the silver nitrate paste 7. The paste 7 is allowed to stay in contact with the endometrium for a predetermined period of time or until the practitioner concludes that sufficient necrosis has taken place by observation through the hysteroscope. The period of time will vary depending on the concentration of the silver nitrate and the depth to which treatment is desired, however, for most applications a period of about 3 to about 15 minutes is preferred. In an especially preferred embodiment, a period of about 4 to about 6 minutes is utilized.

The volume of paste injected should not exceed the natural fill volume of the uterine cavity 4, approximately 5 ml to approximately 15 ml, and the pressure applied in delivering the paste 7 should not result in an internal uterine pressure that exceeds fallopian tubal opening pressure of approximately 40 to 50 mmHg. The means for injecting the silver nitrate paste 7 is preferably fitted with a means to gauge the pressure being applied to the paste, i.e. a manometer, a spring, a pop-off valve or a blister in the wall of the tube or syringe designed to control the pressure to the desired limit. When employing a silver nitrate paste 7, the procedure can be monitored by x-ray or sonography for control of localization and degree of filling.

After sufficient time has elapsed to chemically necrose the endometrium to a depth of approximately 4 mm to about 5 mm, a deactivating agent, e.g., an aqueous solution of sodium chloride 8, preferably about 5% by weight sodium chloride, is introduced through the first catheter 2 under a positive pressure of about 30 to 40 mmHg to deactivate any remaining active silver nitrate paste 7. In an especially preferred embodiment, the carrier is soluble in the deactivating agent. The silver nitrate 7 and sodium chloride 8 will react to form inert silver chloride 10. By washing the uterine cavity 4 with excess aqueous sodium chloride solution 8, e.g., about 2 to 3 liters, complete deactivation of the silver nitrate paste 7 is promoted. Two methods for washing the uterine cavity 4 are preferred. During tidal washing, the sodium chloride solution 8 is delivered and withdrawn through the same catheter, e.g., 3. The sodium chloride solution 8 should be delivered at pressures below fallopian tubal opening pressure to reduce the likelihood of washing any remaining silver nitrate paste 7 into the fallopian tubes 12. After waiting a sufficient period of time for the sodium chloride solution 8 to deactivate the silver nitrate paste 7 into silver chloride 10, the sodium chloride solution 8, silver chloride 10, and any remaining silver nitrate paste 7 may be withdrawn under negative pressure, approximately negative 1 to 2 mmHg, applied to the second catheter 3. The negative pressure should be adjusted to allow for evacuation of the uterine cavity 4 so as to minimize the risk of collapsing the lower end or isthmus.

Alternatively, irrigation washing of the uterine cavity 4 is accomplished via a simultaneous inflow of fresh sodium chloride solution 8 and outflow of used sodium chloride solution 8, silver chloride 10, and any remaining silver nitrate 7. Irrigation washing may be accomplished, e.g., by delivering the fresh sodium chloride wash 8 through the first catheter 2 under positive pressure of approximately 30 to 40 mmHg and withdrawing the outwash through the second catheter 3 under negative pressure of about negative 1 to 2 mmHg. The sodium chloride solution 8 may also be introduced via second catheter 3 and withdrawn via first catheter 2 so as to prevent the introduction into the uterine cavity 4 of any silver nitrate remaining in first catheter 2. Alternatively, the practitioner may remove the contracervical cap, intracervical balloon, an intracervical plug utilized to seal the uterine cavity 4 and allow the washout to exit the uterine cavity 4 around the hysteroscope 1 rather than using negative pressure applied to the first catheter.

Most of the deactivated silver chloride 10 will be washed out of the uterine cavity 4 during the wash procedure and any remaining deactivated silver chloride 10 will be expelled from the body via natural processes.

The activity of the caustic agent is readily controlled by using silver compounds such as silver nitrate and silver thiocyanate or other compounds which can release silver ions. The silver ions react with the sulfides, proteins, and chlorides in cells. Since the sulfides and chlorides are vital to cell metabolism, the reaction results in necrosis of the cells. Another potentially useful agent is iodine which is radiopaque like silver. Compositions containing iodine react with the target tissue as the result of the release of elemental free Iodine and the reaction can be stopped by forming a stable compound, for example, sodium iodide. The advantage of the silver nitrate, however, is that the deactivating agent for the silver ion is the chloride ion found in several solutions used regularly in medicine, e.g., intravenously and intramuscularly, such as normal saline Ringer's solution. The silver nitrate deactivation is the essentially stoichiometric formation of an insoluble non-caustic precipitate. In an especially preferred embodiment, silver nitrate and Dextran 70™ are utilized together because they are easy to work with, are controllable, and are recognized by the medical profession and government regulatory agencies as acceptable agents for human use. Dextran 40™ and 70™ can be used intravenously and intramuscularly and in several organ systems such as the genital tract. Silver Nitrate is used on the skin, upper respiratory tract, lower genital tract, and other locations. The silver ion has a loose but stable binding with the dextran carrier but is pulled off by the consumption of the ion at the tissue sites by binding to anions and protein. The carrier may be made of dextrans or glucose or other sugars used in intravenous solutions but preferably in concentrations sufficient to form gels or pastes. In an especially preferred embodiment, the carrier is soluble in the deactivating agent. The compositions prepared in accordance with this invention have a viscosity that is suitable for their intended purpose at temperatures between about 20° C. and about 37° C., however, the viscosity may be adjusted as specific applications dictate. Alginates, aloe, carboxymethylcellulose, silicones and oxidized cellulose may also be used to form pastes and gels but the dextrans and sugars are the preferred choices because of their acceptance by the medical profession and regulatory agencies.

The speed and severity of the chemical necrosis may be regulated by the percentage of the silver nitrate in the paste. By increasing the percentage of the silver nitrate in the paste the possibility for a deeper burn is increased. It is possible, by procedures well known to those skilled in the art, to determine the appropriate concentration of silver nitrate to achieve the desired depth of cauterization for specific applications. One of the benefits of this invention is that by employing silver nitrate, the practitioner may easily terminate the treatment by introducing a normal saline solution, e.g., NaCl, which will deactivate the silver nitrate by forming silver is chloride. Alternatively, the practitioner could formulate a paste that is essentially self regulating. For example, a weak silver nitrate paste may be formulated that will expend itself after necrosing to a depth of only half the maximum safely allowable depth, thereby reducing the danger of necrosing too deeply.

The viscosity of the caustic composition is adjusted so that it does not flow uncontrollably within the uterus. The caustic composition should flow easily, i.e, without excessive pressure, through a catheter having an inside diameter of about 2 mm. The caustic composition should be thick enough that it does not run, i.e, it stays in the vicinity of the point of application. In a preferred embodiment, a caustic composition having a consistency ranging from toothpaste to pancake syrup is utilized as specific applications dictate. Thixotropic caustic compositions utilizing, e.g., mineral clays or the like, may be especially useful in some applications.

Studies of viscosity showed that about 10 gms of Dextran 70™ mixed with about 10 ml of water containing varying concentrations of silver nitrate flowed slowly and smoothly under pressure through a 2 mm catheter 10 cm to 50 cm long attached to a 10 ml syringe. However, the concentrations may be varied as specific applications dictate to meet the conditions of delivery and the organ or structure to be treated. The low viscosity or "watery" compositions comprise about 5 gms of Dextran 70™ and about 10 ml $H_2O$ and the high viscosity or "thick pastel" compositions are comprised of about 10 gms to about 15 gms or higher of Dextran 70™ and about 10 ml $H_2O$.

The concentrations of silver nitrate utilized in practising this invention are higher than those concentrations of silver nitrate generally employed in conventional dermatologic pastes and bladder irrigation compositions which often contain silver nitrate in an amount ranging from about 1% to about 20% by weight. (One exception is the conventional silver nitrate stick which is often pure silver nitrate precipitated on an applicator stick for use in the vagina, skin, nose and other superficial places to cauterize bleeding or abraded areas.) In a preferred embodiment of this invention, the concentrations of caustic agent utilized for selective tissue destruction ranges from about 5 grams per 10 ml of water to a substantially saturated solution of about 16.5 grams per 10 ml of water at about 25° C. In an especially preferred embodiment, the concentrations of caustic agent utilized ranges from about 7–8 gm/10 ml of water. In an especially preferred embodiment, the composition comprises about 40% by weight silver nitrate, about 30% by weight dextran, and about 30% by weight water. In another especially preferred embodiment, the composition comprises about 45% by weight silver nitrate, about 28% by weight dextran, and about 28% by weight water. The reason that higher concentrations of silver nitrate are preferred is that much of the silver ion is taken up by, i.e., reacts with, tissue chlorides, sulfides, and proteins. Thus, high concentrations are needed to compensate for the deactivation of much of the silver ion in the extracellular spaces in order to effect tissue destruction of the endometrium to the desired depth of about 4 to about 5 mm. These higher concentrations produce the desired tissue protein damage and mitochondrial and nuclear damage which have been confirmed by microscopic observation. These reactions can be selectively and rapidly arrested in a controlled manner by the introduction of saline solution which rapidly deactivates residual free silver nitrate by forming silver chloride.

Bacteriologic studies of the mixture of silver nitrate and Dextran 70™ prepared in accordance with this invention show that the pastes are sterilized by the presence of the silver nitrate. The dextrans support bacterial growth while the silver/dextran mixtures show no bacterial growth. Chemical analyses of the silver nitrate in dextran using atomic absorption spectrometry show the silver ion to be loosely bound (about 75%) to the dextrans and that the binding remained constant over a period of at least one week.

Specific embodiments of the invention will now be illustrated by the following examples.

EXAMPLE 1

A mixture of about 15 gms of silver nitrate, about 10 gms of Dextran 70™, and about 10 gm. of water was prepared and injected via a cervical catheter into two normal uterine specimens immediately following hysterectomy. The composition was sufficiently flowing (fluid) to spread out to fill substantially the uterine cavity under high pressure, e.g., about 200 mm of mercury, but was sufficiently viscous so that it did not flow into the fallopian tubes which have an opening with a diameter of about 1 mm. This composition was left in the uterus for about 10 minutes and produced the desired histologic damage to a depth of about 4 mm to about 5 mm into the uterine wall. Chemical activity of the mixture was arrested at about 10 minutes by normal saline irrigation which caused a silver chloride precipitate to form and permitted a washout of the dextran silver nitrate/silver chloride mixture from the uterine cavity.

EXAMPLE 2

The composition used in EXAMPLE 1 was also tested in in vivo rabbit uteri and the silver nitrate/dextran paste again produced the desired extended rapid destruction which was quickly arrested by normal saline as previously discussed. In addition, the use of normal saline in the area surrounding the uterine horns during the laparotomy to test the paste in the horns effectively protected the adjacent organs from the effects of the silver nitrate spill.

EXAMPLE 3

A series of four adult female rabbits was anesthetized and laparotomy performed to expose the genital tract. The first animal had one uterine horn serve as a control. The other uterine horn was injected with a Dextran 70™ paste comprising about 10 gms of dextran, about 9 gms of silver nitrate and about 10 ml. of water. The composition was injected using a syringe and an 18 gauge needle and the tissues contacted by the paste instantly showed reaction. Some of the paste spilled into the peritoneal cavity. The area of bowel and bladder and peritoneal surface which made contact with the paste was treated with normal saline which caused a white precipitate. The second rabbit was treated similarly except that both uterine horns were treated. Spill again occurred and was blocked by saline. The third rabbit was treated in the same fashion but saline was poured into the pelvis prior to injection. Spill occurred again, however, because the pelvis had been pre-treated with saline, the spill never reacted with the surrounding tissues. The fourth rabbit was treated like the third except that only one horn was injected. The animals were closed and returned to the cages. Rabbit one died that night, probably from the surgery and anesthesia. Autopsy showed an acute inflammatory reaction of the uterine horns and pelvic tissues. Rabbit two died seven days later. Autopsy showed acute and chronic reaction in the horns which were thoroughly damaged as well as pelvic inflammation with probable bowel perforation from the chemical injury. Rabbits three and four were killed at three weeks after a normal recovery. Autopsy showed no reaction or adhesions of the bowel or peritoneal tissues. It is believed that this is because the peritoneal cavity had been protected by saline before the silver nitrate spill came in contact with the tissues. The uterine horns showed the desired result, i.e., inflammation and ablation to a desired level and destruction of endometrium and early scarring. The initial injection into the uterine horns was arrested by the injection of normal saline after six and ten minutes. This time difference did not make a pathological difference as the silver nitrate composition of the mixture was strong and selected from the experience with human uterine specimens which were very thick compared to the thin and small rabbit uterine horns. The rabbit uterine horns were badly damaged in the treated areas and normal in the untreated areas. Thus, the reaction is focal, localized, and can be controlled in intensity and duration. Photos were taken and microscopic pathology obtained which showed destruction of the endometrium to the desired depth of about 4 mm to about 5 mm.

The compositions of this invention have been shown to be pharmacologically active in an amount sufficient to chemically necrose tissue and can be selectively and rapidly controlled and arrested after use with saline solutions to stop the reaction and during use to limit the locus of the destructive effect from unintended damage to surrounding non-target tissues and organs. The compositions are bacteriologically sterile and the viscosity can be manipulated to the desired viscosity by the amount of water added. Hence their delivery can be controlled by volume, pressure and viscosity.

The compositions of this invention are not limited to the applications discussed above and have additional wide applicability in the medical field. The mixture of silver ion with the carriers makes possible controlled delivery of the caustic agent to a wide range of target organs and structures, e.g., the endometrium for endometrial ablation, a colonic polyp during colonoscopy, a bladder polyp during cystoscopy, ablation of a small bladder diverticulum, ablation of the gall bladder via a choledochoscope with X-ray and sonographic control, destruction of bronchial lesions at bronchoscopy, and other minimally invasive approaches. Indeed, the compositions and method of this invention provide an alternative to mechanical, electrosurgical or laser destruction of targeted tissues and organs under open, endoscopic, monographic or radiographic control. The use of physiologic saline solutions permits controlled arrest of the reaction as well as protection of non-targeted tissues and organs in the zone of treatment. The carriers provide a delivery vehicle for the active agent and can be washed away, as they are water soluble, or can be metabolically removed in the cases of sugars and dextrans.

In an alternative embodiment, the compositions of this invention can also serve as delivery vehicles for other therapeutic agents or medicaments, such as selected antibiotics or anti-inflammatory agents, e.g., cortisone, hydrocortisone, or prednisone which could be used simultaneously with the active chemical ablation or before or after such ablative intervention. The above effects have applicability in human medicine as well as in veterinary medicine, particularly because the chemical mixtures will assume the shape of hollow organs to be treated and individual to individual or species to species variation can be adjusted by volume, viscosity, pressure, treatment time and concentration of the active agent. In a preferred embodiment, the therapeutic agent or medicament may be delivered to the area to be treated by catheter either blindly or under sonographic, visual, or radiographic observation.

It has been demonstrated that the compositions of this invention will in general cause severe caustic reactions to the cells of target tissues and necrose them and that saline will block the reaction as well as protect vital non-target tissues if appropriately used. Thus, the principle of utilizing caustic agents in controlled doses, for controlled periods of time, in conjunction with suitable deactivating agents has been demonstrated to be successful in producing an intended injury while restricting it to the target tissues only.

The compositions of this invention also provide for the delivery of other non-tissue destroying agents such as anti-inflammatory agents, e.g., cortisone, which could be delivered in high concentrations for local short term effect (1–7 days). These non-tissue destroying compositions provide a means of inhibiting the unwanted formation of adhesions following, e.g., myomectomy, tubal repair, joint repair, etc.

The technique may be used to treat other body cavities by varying the ingredients and percentages of ingredients in the composition, varying the viscosity, and varying the time of treatment as specific applications dictate.

In a preferred embodiment, the composition has a viscosity which allows it to be introduced to the target area via a hysteroscope and allows the composition to remain in contact with the target tissue in an amount and for a period of time sufficient to effect chemical necrosis. In an especially preferred embodiment, the composition is fluid enough to be introduced via a 2 mm to 3 mm catheter to the uterus and sufficiently viscous so as not to flow into the uterine cavity at a pressure of about 80 mmHg.

It is envisioned that a variety of caustic agents and their respective deactivating agents may be used in this process. Caustic agents such as zinc chloride, phenol, iodine KOH, NaOH, and various acids and alkalies are well known in the art and are applicable to the methods of this invention and may be deactivated by chemical reaction, removal, dilution or dosimetry.

It is also envisioned that in place of the second catheter of the first and second embodiments, the neutralizing solution may be delivered through the first catheter. In this embodiment, the volume of deactivating solution employed must be adjusted to account for the residual caustic paste that remains in the first catheter that will itself need to be deactivated.

In an especially preferred embodiment of the invention, the viscosity of the saline washout solution 8 is also adjusted by increasing the viscosity, e.g., to a "creamy" viscosity similar to the viscosity of, e.g., conventional skin moisturizing lotions or suntan lotions, so as to reduce the likelihood that the inactivated silver nitrate, i.e., silver chloride 10, will be introduced into non-target areas, e.g., the fallopian tubes or the bloodstream of the patient. Increasing the viscosity of the saline washout solution or washout lotion 8 prevents the paste 7 from developing too low a viscosity, i.e., it prevents the caustic paste 7 from becoming too thin or "runny" during the washout step, and thus, reduces the likelihood that the neutralized silver nitrate, i.e., silver chloride 10, will infuse into the fallopian tubes or the vascular system during the neutralization and washout steps.

In an especially preferred embodiment, the washout solution or washout lotion 8 used to neutralize and wash out the silver chloride comprises about 32% by weight to about 40% by weight dextran and about 60% to about 68% by weight normal saline and has a viscosity of between about 220 to about 600 centipoise.

The caustic paste 7 is preferably introduced into the uterus at a pressure that is about equal to or less than about 200 mmHg. During the washout of the paste 7 with the washout solution or washout lotion 8 the intrauterine pressure should be maintained at a pressure about equal to or less than about 40 mmHg so as to further reduce the likelihood that the silver chloride 7 will infuse into the bloodstream or enter non-target areas. If continuous flow irrigation is utilized, an inflow pressure of about 40 mmHg and an outflow pressure of about 0 to about −5 mmHg is preferred.

Figure 2:
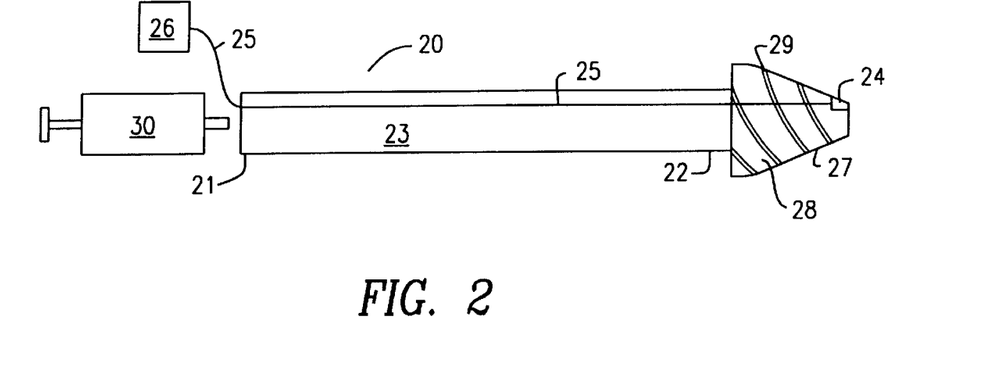
FIG. 2 shows a caustic paste and washout solution or washout lotion delivering cannula constructed in accordance with the invention.

FIG. 2 shows a caustic paste and washout solution or washout lotion delivering cannula 20 constructed in accordance with the invention. The cannula 20 has a proximal end 21 and a distal or injection end 22 and a longitudinal bore 23 therethrough. The proximal end 21 is adapted to form a substantially fluid tight seal with a caustic paste 7 introduction means, e.g., a syringe 30. A means for measuring pressure 24 is disposed at the distal or injection end 22 of the cannula 20 and is adapted and disposed so as to measure the internal pressure of the uterine cavity 4. Because the pressure of injection is higher at the proximal end 21 of the injection cannula 20, in order to overcome the Pousielle forces of resistance to movement of the caustic paste 7, disposing the means for measuring pressure 24 at or near the distal end 22 of the injection cannula 20 will provide a more accurate measurement of the internal pressure of the uterine cavity 4. The means for measuring pressure 24 may be selected from a wide variety of means well known to those skilled in the art as suitable for this purpose, however, in a preferred embodiment a pressure monitor or transducer is utilized. The means for measuring pressure 24 communicates via wire lead 25 with control means 26 provided for displaying the internal pressure of the uterus 13, for limiting the pressure at which the caustic paste 7 is introduced into the uterine cavity 4, and for limiting the pressure at which the washout solution or washout lotion 8 is introduced into the uterine cavity 4.

As shown in FIG. 2, the tip 27 disposed at the distal end 22 is provided with a shape, e.g., a conical or olive tip shape, so as to facilitate insertion into the cervix 9 and the formation of a substantially fluid tight seal when the tip 27 is disposed in the cervix 9 so as to reduce the likelihood that the caustic paste 7 will leave the uterine cavity 4 and enter the vaginal canal 102. In an especially preferred embodiment, the external surface 28 of the tip 27 is provided with spiral grooves 29 or a corkscrew configuration on its outer surface 28 to enhance the seal between the outer surface 28 of the tip 27 and the cervix 9. When this embodiment of the invention is utilized, after the caustic paste 7 has been introduced into the uterine cavity 4, the paste delivery cannula 20 is withdrawn from the cervix 9 and a clean cannula 20 is inserted into the cervix 9. A clean syringe 30 filled with washout solution or washout lotion 8 is attached to the proximal end 21 of the cannula 20 and the washout solution or washout lotion 8 is introduced into and withdrawn from the uterine cavity 4 using the syringe 30.

Figure 3A:
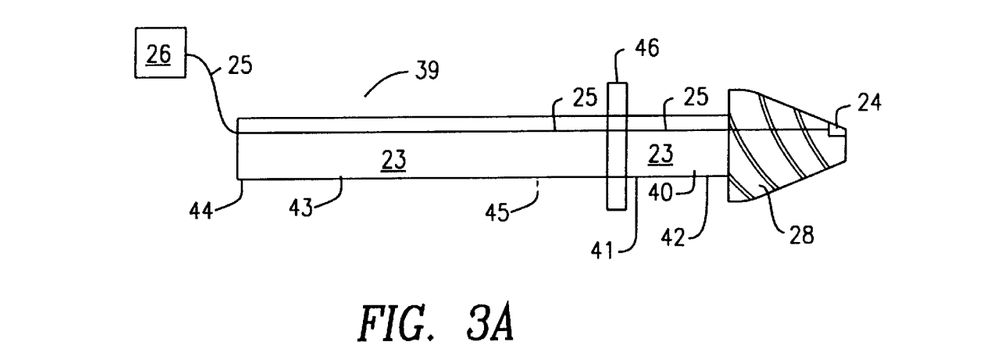
FIG. 3A shows an alternative embodiment of the cannula shown in FIG. 2.
Figure 3B:
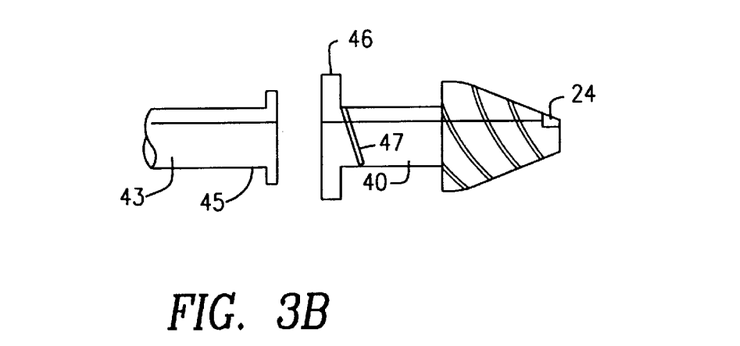
FIG. 3B shows an alternative embodiment of the cannula shown in FIG. 2.

FIGS. 3A and 3B show an alternative embodiment of the cannula shown in FIG. 2. In the embodiment shown in FIGS. 3A and 3B, the cannula 39 comprises a first portion cannula 40 having a proximal end 41 and a distal end 42 and a second portion cannula 43 having a proximal end 44 and a distal end 45. A coupling 46 is disposed between the proximal end 41 of the first portion cannula 40 and the distal end 45 of the second portion cannula 43 as shown in FIG. 3A. The coupling 46 is preferably disposed on the proximal end 41 of the first portion cannula 40 as shown in FIG. 3B. The coupling 46 is adapted to provide a substantially fluid tight seal between the first portion 40 and the second portion 43 and is also adapted to provide communication between the wire lead 25 disposed on the first portion 40 communicating with the pressure sensing means 24 and the wire lead 25 disposed on the second portion 43 communicating with the pressure display means and control means 26. The coupling 46 may be selected from a wide range of couplings well known to those skilled in the art as suitable for this purpose, for example a friction fit or a male/female interlock, however, in a preferred embodiment a leuer lock is utilized. A means, e.g., a plunger means, may be provided at the proximal end 44 of the second portion cannula 43 for facilitating the engagement and disengagement of the second portion cannula 43 from the coupling means 46 disposed on the proximal end 41 of the first portion cannula 40. In an especially preferred embodiment, the coupling means 46 is provided with a valve 47 (shown in FIG. 3B) that blocks the longitudinal bore 23 of the first portion cannula 40 when the second portion cannula 43 is disengaged from the coupling means 46. This valve 47 helps maintain the desired pressure in the uterine cavity 4 and further reduces the likelihood of leakage of caustic paste into the vaginal canal 102. In operation when this embodiment is utilized, the proximal end 41 of the first portion cannula 40 is connected to the distal end 45 of the second portion cannula 43 via the coupling 46. The tip 27 of the first portion cannula 40 is then inserted into the vaginal canal 102 and the tip 27 is advanced and inserted into the cervix 9 to form a substantially fluid tight seal between the outer surface 28 of the tip 27 and the cervix 9. In a preferred embodiment, the washout solution or washout lotion 8 is then introduced into the vaginal canal 102 to protect the vaginal tissues from any caustic paste 7 that might inadvertently be introduced into the vaginal canal 102 during the procedure. A syringe 30 containing the caustic paste 7 is then attached to the proximal end 44 of the second portion cannula 43 and the caustic paste 7 is introduced into the uterine cavity 4 under controlled pressure as previously discussed. The second portion catheter 43 may then be disengaged from the coupling means 46 and removed from the vaginal canal 102. A clean second portion or washout cannula 43 is then inserted into and advanced in the vaginal canal 102 and the distal end 45 is engaged to the coupling 46. A syringe 30 is then connected to the proximal end 44 of the clean second portion or washout cannula 43 and washout solution or washout lotion 8 is introduced into the uterine cavity 4 and allowed to remain within the uterine cavity 4 for a period of time sufficient to neutralize the caustic paste 7. The syringe 30 is then used to withdraw the neutralized and diluted paste 10 from the uterine cavity 4 as previously discussed.

Figure 4:
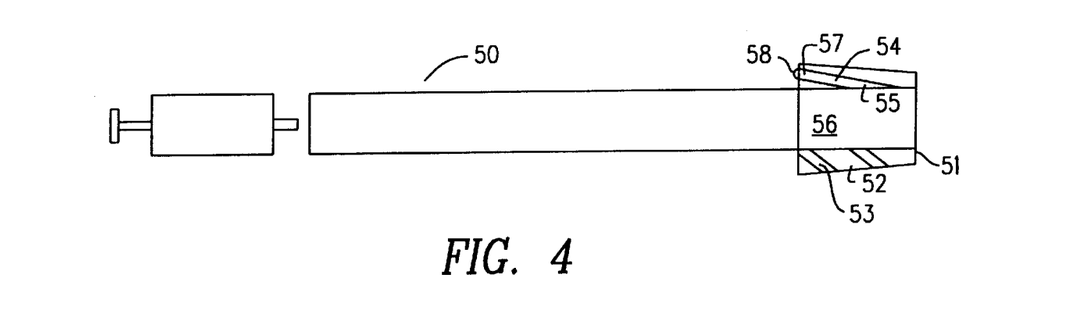
FIG. 4 shows an alternative embodiment of a caustic paste introducing cannula construced in accordance with the invention.

FIG. 4 shows an alternative embodiment of a caustic paste introducing cannula 50 constructed in accordance with the invention. As shown in FIG. 4, the tip 51 is provided with a shape, e.g., a conical or olive tip shape, so as to facilitate entrance into the cervix 9 and the formation of a substantially fluid tight seal when the tip 51 is disposed in the cervix 9 so as to reduce the likelihood that the caustic paste 7 will leave the uterine cavity 4 and enter the vaginal canal 102. In an especially preferred embodiment, the external surface 52 of the tip 51 is provided with spiral grooves 53 or a corkscrew configuration on its outer surface 52 to enhance the seal as previously discussed. The tip 51 is provided with a channel 54 having a distal end 55 in fluid communication with the longitudinal bore 56 of the cannula 50 and a proximal end 57 in fluid communication with a pop-off blister 58 to control the pressure of the caustic paste 7 within the uterine cavity 4. In a preferred embodiment in a cannula 50 used to introduce the caustic paste 7, the pop-off blister 58 is set at about 100 mmHg. Thus, if the pressure in the uterine cavity 4 exceeds about 100 mmHg, the pop-off blister 58 will "pop" or open relieving the pressure in the uterine cavity 4 and allowing the caustic paste to enter the vaginal canal 102 which has preferably been previously protected by the introduction of washout solution or washout lotion 8. After the caustic paste 7 has been introduced into the uterine cavity 4, the cannula 50 is removed. A second clean cannula or washout cannula 50' is then inserted into the cervix 9 as previously discussed so that washout solution or washout paste 8 can be introduced into the uterine cavity 4.

Figure 5:
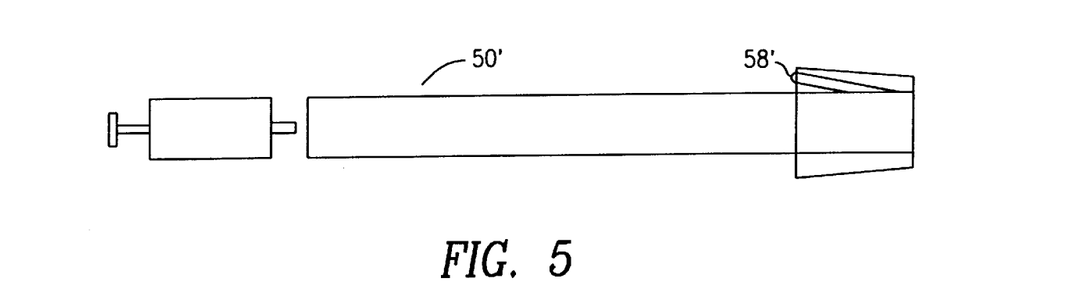
FIG. 5 shows an alternative embodiment of the cannula shown in FIG. 4.

FIG. 5 shows the cannula of FIG. 4 which has been modified for use in a tidal washout system to wash out the neutralized and diluted caustic paste 10. The washout solution or washout lotion 8 is injected into the uterine cavity 4 and allowed to remain within the uterine cavity 4 for a period of time sufficient to neutralize the caustic paste 7. The neutralized and diluted paste 10 is then withdrawn using the syringe. The second clean cannula or washout cannula 50' is similar in design to the first cannula 50 with the exception that the pop-off blister 58' is set at about 60 mmHg because of the lower pressure desired during washout as previously discussed. Thus, if the pressure in the uterine cavity 4 exceeds about 60 mmHg during washout, the pop-off blister 58' will "pop" or open relieving the pressure in the uterine cavity 4 allowing the neutralized paste to enter the vaginal cavity 102.

Figure 6:
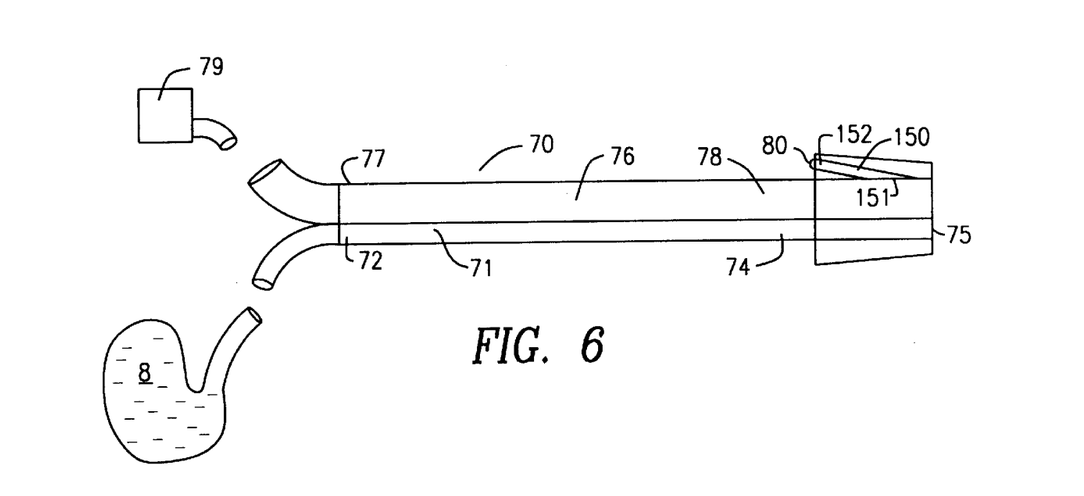
FIG. 6 shows a double lumen washout cannula constructed in accordance with the invention.

FIG. 6 shows a double lumen washout cannula 70 constructed in accordance with the invention for use in a continuous flow washout system. The cannula 70 is provided with a first lumen 71 having a proximal end 72 in fluid communication with a source of washout solution or washout lotion 8 and a distal end 74 in fluid communication with the tip opening 75. In a preferred embodiment, the first lumen 71 has a diameter of about 2 mm. The cannula 70 is also provided with a second lumen 76 having a proximal end 77 and a distal end 78. The distal end 78 is in fluid communication with the tip opening 75 and the proximal end 77 is in fluid communication with a means 79 for withdrawing the neutralized and diluted caustic paste. In a preferred embodiment, the second lumen 76 has a diameter that is equal to or greater than about 5 mm and the means 79 for withdrawing the neutralized caustic paste 10 is adapted to withdraw the neutralized caustic paste 10 at a pressure of about 0 to about −5 mmHg of negative pressure. The tip 75 is provided with a channel 150 having a distal end 151 in fluid communication with the longitudinal bore 78 of the cannula and a proximal end 152 in fluid communication with a pop-off blister 80 to control the pressure of the washout solution or washout lotion 8 within the uterine cavity 4. In a preferred embodiment, the pop-off blister 80 is set at about 60 mmHg or less as previously discussed.

Figure 7:
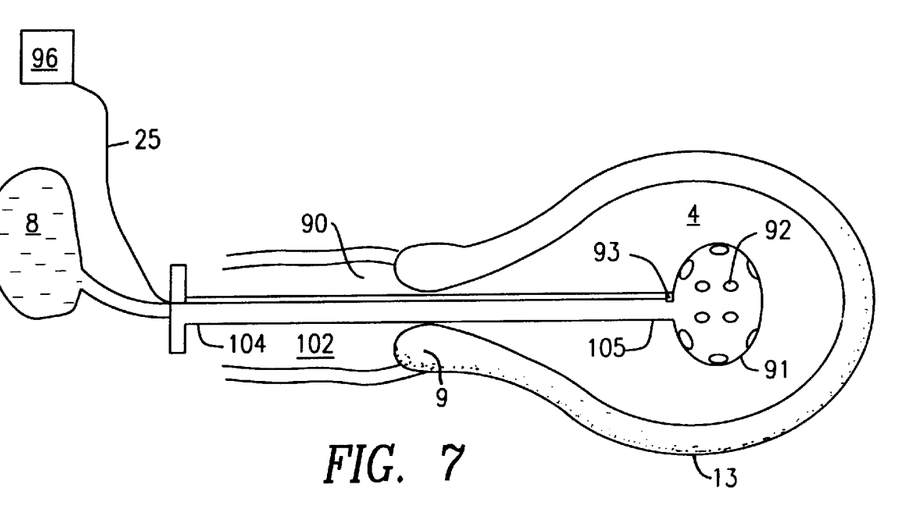
FIG. 7 shows a washout cannula constructed in accordance with the invention.

FIG. 7 shows a cannula 90 having a proximal end 104 and a distal end 105 constructed in accordance with the invention for use in a catheter washout system. In this embodiment, the tip 91 disposed at the distal end 105 is provided with a plurality of apertures 92 to optimize the distribution of the washout solution or washout lotion 8 which in a preferred embodiment is introduced at a pressure of about 60 mmHg or less. A pressure sensing means 93, in communication with a control means 96, may be disposed on the tip 91 or distal end 105. The low viscosity washout solution or washout lotion 8 may be gently irrigated into the uterine cavity 4 by moving or reciprocating the cannula 90 within the uterine cavity 4. The control means 96 is adapted to control the pressure at which the washout solution or washout lotion 8 is introduced into other uterine cavity 4. This embodiment and method is especially preferred where the viscosity of the washout solution or washout lotion 8 is high, e.g., about equal to or greater than about 1,000 centipoise. The cannula 90 is sized so as to have a diameter that is smaller than is required to form a substantially fluid tight seal with the cervix 9, thus, permitting the neutralized and diluted caustic paste 10 to leave the uterine cavity 4 via the space between the catheter 90 and the cervix 9.

Figure 8:
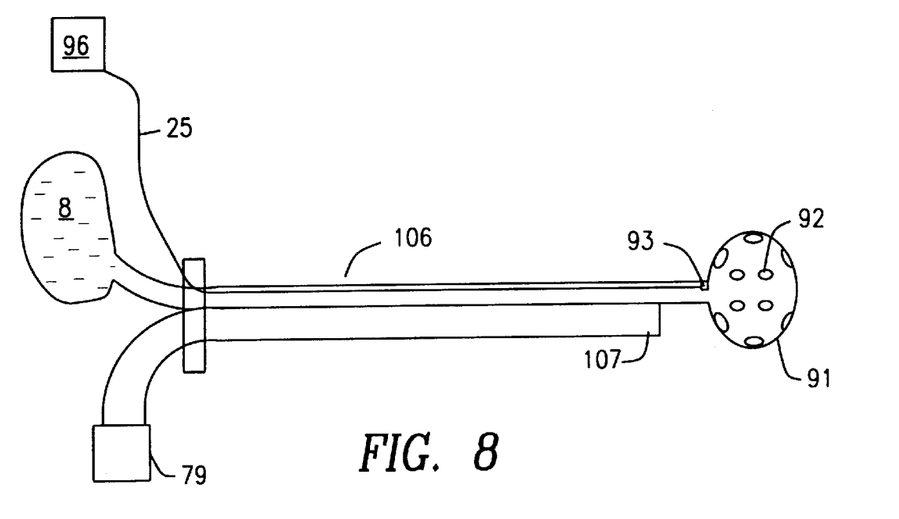
FIG. 8 shows an alternative embodiment of the cannula shown in FIG. 7.

FIG. 8 shows an alternative embodiment of the cannula shown in FIG. 7. As shown in FIG. 8, the cannula 106 has been provided with a second lumen 107 which is connected to a means 79 for applying negative pressure to facilitate the removal of the neutralized and diluted paste 10 from the uterine cavity 4.

What is claimed is:

1. A method for treating the menorrhagia, comprising the steps of:
   a) applying a caustic composition to the endometrium of a uterus;
   b) allowing said caustic composition to remain in contact with said endometrium for a period of time sufficient to effect chemical necrosis of said endometrium;
   c) contacting said caustic composition with a deactivating agent to deactivate said caustic composition and rapidly stop necrosis; and
   d) withdrawing said deactivated caustic composition and said deactivating agent from said uterus.

2. A method for treating menorrhagia, comprising the steps of:
   a) applying a silver nitrate composition to the endometrium of a uterus;
   b) allowing said silver nitrate composition to remain in contact with said endometrium for a period of time sufficient to effect chemical necrosis of said endometrium;
   c) contacting said silver nitrate composition with sodium chloride to deactivate said silver nitrate composition and rapidly stop necrosis; and d) withdrawing said deactivated silver nitrate composition and said sodium chloride from said uterus.

3. A method for treating the lining of a body cavity while protecting non-target tissue, comprising the steps of:
   a) applying a non-caustic deactivating agent to said non-target tissue, said deactivating agent selected to deactivate the caustic composition applied in step b);
   b) applying a caustic composition to said lining;
   c) allowing said caustic composition to remain in contact with said lining for a period of time sufficient to effect chemical necrosis of said lining;
   d) contacting said caustic composition with a deactivating agent composition to deactivate said caustic composition and rapidly stop necrosis, said deactivating agent comprising about 32% by weight to about 40% by weight dextran and about 60% to about 68% by weight normal saline and having a viscosity of between about 220 to about 600 centipoise; and
   e) withdrawing said deactivated caustic composition and said deactivating agent from said body cavity.

4. The method of claim 3, wherein the caustic composition is allowed to remain in contact with the endometrial mucosa for about 3 to about 15 minutes.

5. The method of claim 4, wherein the caustic composition is allowed to remain in contact with the endometrial mucosa for about 4 to about 6 minutes.

6. The method of claims 3, further comprising the step of regulating the pressure at which the caustic composition is applied so that the pressure is sufficiently high so as to increase the likelihood that the caustic composition will make substantially uniform and intimate contact with the endometrial mucosa and so that the pressure is sufficiently low so as to reduce the likelihood that the caustic composition will enter the fallopian tubes.

7. The method of claim 6, wherein the pressure is regulated to a pressure of about 40 to about 50 mm Hg.

8. The method of claim 3 wherein the withdrawing step is carried out using a method selected from the group consisting of tidal flow, continuous sodium chloride rinsing, and irrigation washing.

9. A kit for treating the endometrial mucosa of a uterus, comprising:
   a) a chemical cauterizing paste composition comprising:
      a) about 10% to about 50% by weight caustic agent;
      b) about 30% to about 80% by weight inert carrier; and
      c) about 0% to about 55% weight $H_2O$, wherein the viscosity of said composition has been adjusted so that said composition will remain in contact with the endometrial mucosa in an amount and for a period of time sufficient to effect chemical necrosis, the paste composition having a viscosity sufficiently fluid so as to cover substantially all of the endometrial mucosa and sufficiently viscous so as to reduce the likelihood that the paste composition will enter the fallopian tubes; and
   b) a neutralizing agent, said neutralizing agent comprising about 32% by weight to about 40% by weight dextran and about 60% by weight to about 68% by weight normal saline and having a viscosity of between about 220 to about 600 centipoise.

10. The kit of claim 9, wherein the caustic agent is silver nitrate and the inert carrier is dextran.

11. The kit of claim 10, further comprising a hysteroscope provided with: means for applying the paste composition to the endometrial mucosa of the uterus; means for introducing a fluid medium into the uterus to expand the uterus; means for introducing the neutralizing agent into the uterus; means for withdrawing the neutralized paste composition from the uterus; and means for monitoring the pressure exerted by the paste composition against the endometrial mucosa.

12. The kit of claim 11, wherein the means for monitoring the pressure exerted by the paste composition against the endometrial mucosa is selected from the group consisting of: a manometer, a spring, a pop-off-valve, and a blister.

13. The kit of claim 11, wherein the hysteroscope is further provided with means for observing the steps of the procedure.

14. A kit for treating the endometrial mucosa of a uterus, comprising:
   a) a chemical cauterizing paste composition comprising:
      a) about 43% by weight silver nitrate;
      b) about 29% by weight dextran; and
      c) about 29% weight $H_2O$,
      wherein the viscosity of the paste composition has been adjusted so that the paste composition will remain in contact with the endometrium in an amount and for a period of time sufficient to effect chemical necrosis, the paste composition having a viscosity sufficiently fluid so as to cover substantially all of the endometrial mucosa and sufficiently viscous so as to reduce the likelihood that the paste composition will enter the fallopian tubes; and
   b.) an aqueous sodium chloride solution for neutralizing the silver nitrate to substantially inert silver chloride, said sodium chloride solution comprising about 32% by weight to about 40% by weight dextran and about 60% to about 68% by weight normal saline and having a viscosity of between about 220 to about 600 centipoise.

15. The kit of claim 14, further comprising a hysteroscope provided with: means for applying the paste composition to the endometrial mucosa of the uterus; means for introducing a fluid medium into the uterus to expand the uterus; means for introducing the neutralizing agent into the uterus; means for withdrawing the neutralized paste composition from the uterus; and means for monitoring the pressure exerted by the paste composition against the endometrial mucosa.

16. The kit of claim 15, wherein the means for monitoring the pressure exerted by the paste composition against the endometrial mucosa is selected from the group consisting of: a manometer, a spring, a pop-off-valve, and a blister.

17. The kit of claim 15, wherein the hysteroscope is further provided with means for observing the steps of the procedure.

18. A kit for treating the endometrial mucosa of a uterus, comprising:
   a) a chemical cauterizing paste composition, comprising:
      a) about 31% by weight silver nitrate;
      b) about 34% by weight dextran; and
      c) about 34% weight $H_2O$,
      wherein the viscosity of said paste composition has been adjusted so that said composition will remain in contact with the endometrium in an amount and for a period of time sufficient to effect chemical necrosis, the paste composition having a viscosity sufficiently fluid so as to cover substantially all of the endometrial mucosa and sufficiently viscous so as to reduce the likelihood that the composition will enter the fallopian tubes; and
   b) an aqueous sodium chloride solution for neutralizing the silver nitrate to substantially inert silver chloride said sodium chloride solution comprising about 32% by weight to about 40% by weight dextran and about 60% to about 68% by weight normal saline and having a viscosity of between about 220 to about 600 centipoise.

19. The kit of claim 18, further comprising a hysteroscope provided with: means for applying the paste composition to the endometrial mucosa of the uterus; means for introducing a fluid medium into the uterus to expand the uterus; means for introducing the neutralizing agent into the uterus; means for withdrawing the neutralized paste composition from the uterus; and means for monitoring the pressure exerted by the paste composition against the endometrial mucosa.

20. The kit of claim 19, wherein the means for monitoring the pressure exerted by the paste composition against the endometrial mucosa is selected from the group consisting of: a manometer, a spring, a pop-off-valve, and a blister.

21. The kit of claim 19, wherein the hysteroscope is further provided with means for observing the steps of the procedure.

22. A kit for treating the endometrial mucosa of a uterus, comprising:
   a.) a chemical cauterizing paste composition, comprising:
      a) about 40% by weight silver nitrate;
      b) about 30% by weight dextran; and
      c) about 30% weight $H_2O$,
   wherein the viscosity of said paste composition has been adjusted so that said paste composition will remain in contact with the endometrium in an amount and for a period of time sufficient to effect chemical necrosis, the paste composition having a viscosity sufficiently fluid so as to cover substantially all of the endometrial mucosa and sufficiently viscous so as to reduce the likelihood that the composition will enter the fallopian tubes; and
   b) an aqueous sodium chloride solution for neutralizing the silver nitrate to substantially inert silver chloride said sodium chloride solution comprising about 32% by weight to about 40% by weight dextran and about 60% to about 68% by weight normal saline and having a viscosity of between about 220 to about 600 centipoise.

23. The kit of claim 22, further comprising a hysteroscope provided with: means for applying the paste composition to the endometrial mucosa of the uterus; means for introducing a fluid medium into the uterus to expand the uterus; means for introducing the neutralizing agent into the uterus; means for withdrawing the neutralized paste composition from the uterus; and means for monitoring the pressure exerted by the paste composition against the endometrial mucosa.

24. The kit of claim 23, wherein the means for monitoring the pressure exerted by the paste composition against the endometrial mucosa is selected from the group consisting of: a manometer, a spring, a pop-off-valve, and a blister.

25. The kit of claim 23, wherein the hysteroscope is further provided with means for observing the steps of the procedure.

26. A kit for treating the endometrial mucosa of a uterus, comprising:
   a.) a chemical cauterizing paste composition, comprising:
      a) about 45% by weight silver nitrate;
      b) about 28% by weight dextran; and
      c) about 28% weight $H_2O$
   wherein the viscosity of said paste composition has been adjusted so that said paste composition will remain in contact with the endometrium in an amount and for a period of time sufficient to effect chemical necrosis, the paste composition having a viscosity sufficiently fluid so as to cover substantially all of the endometrial mucosa and sufficiently viscous so as to reduce the likelihood that the paste composition will enter the fallopian tubes; and
   b) an aqueous sodium chloride solution for neutralizing the silver nitrate to substantially inert silver chloride, said sodium chloride solution comprising about 32% by weight to about 40% by weight dextran and about 60% to about 68% by weight normal saline and having a viscosity of between about 220 to about 600 centipoise.

27. The kit of claim 26, further comprising a hysteroscope provided with: means for applying the paste composition to the endometrial mucosa of the uterus; means for introducing a fluid medium into the uterus to expand the uterus; means for introducing the neutralizing agent into the uterus; means for withdrawing the neutralized paste composition from the uterus; and means for monitoring the pressure exerted by the paste composition against the endometrial mucosa.

28. The kit of claim 27, wherein the means for monitoring the pressure exerted by the paste composition against the endometrial mucosa is selected from the group consisting of: a manometer, a spring, a pop-off-valve, and a blister.

29. The kit of claim 11, wherein the hysteroscope is further provided with means for observing the steps of the procedure.

30. The kit of claim 9, wherein the inert carrier is soluble in the neutralizing agent.

* * * * *